United States Patent
Woldt et al.

(10) Patent No.: US 10,577,479 B2
(45) Date of Patent: Mar. 3, 2020

(54) TRIPENTYL ESTERS OF TRIMELLITIC ACID

(71) Applicants: Benjamin Woldt, Bochum (DE); Michael Grass, Haltern am See (DE); Florian Boeck, Muenster (DE)

(72) Inventors: Benjamin Woldt, Bochum (DE); Michael Grass, Haltern am See (DE); Florian Boeck, Muenster (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/278,838

(22) Filed: Sep. 28, 2016

(65) Prior Publication Data

US 2017/0088691 A1 Mar. 30, 2017

(30) Foreign Application Priority Data

Sep. 28, 2015 (EP) .................... 15187128

(51) Int. Cl.
*C08K 5/12* (2006.01)
*C07C 67/08* (2006.01)
*C07C 69/76* (2006.01)
*C08K 5/00* (2006.01)
*C07C 67/12* (2006.01)

(52) U.S. Cl.
CPC .............. *C08K 5/12* (2013.01); *C07C 67/08* (2013.01); *C07C 67/12* (2013.01); *C07C 69/76* (2013.01); *C08K 5/0016* (2013.01)

(58) Field of Classification Search
CPC ........ C08K 5/12; C08K 5/0016; C07C 67/08; C07C 69/76; C07C 67/12
USPC ........................................................ 524/311
See application file for complete search history.

(56) References Cited

U.S. PATENT DOCUMENTS

2005/0038285 A1 2/2005 Maschmeyer et al.

FOREIGN PATENT DOCUMENTS

JP 2003-165881 6/2003

OTHER PUBLICATIONS

Drechsler et al.,"Trimellitic and isophthalic acids and their esters," Journal für Praktische Chemie, vol. 27, Issue 5-6, pp. 231-238 (Year: 1965).*
Office Action dated Jun. 20, 2018 in Taiwanese Patent Application No. 105130863.

* cited by examiner

Primary Examiner — Josephine L Chang
(74) Attorney, Agent, or Firm — Oblon, McClelland, Maier & Neustadt, L.L.P.

(57) ABSTRACT

Tripentyl esters of trimellitic acid, especially mixtures of triisopentyl esters of trimellitic acid comprising isomeric pentyl radicals in which more than 5 mol % of the isomeric pentyl radicals incorporated in the ester mixture are branched, have good compatibility with PVC and PVC-containing polymers and simultaneously exhibit a lesser tendency to migrate.

11 Claims, 1 Drawing Sheet

Numbering of the carbon atoms in the different pentyl radicals

Numbering of the carbon atoms in the different pentyl radicals

TRIPENTYL ESTERS OF TRIMELLITIC ACID

BACKGROUND OF THE INVENTION

Field of the Invention

The present invention relates to tripentyl esters of trimellitic acid, to the preparation and use thereof as plasticizers or as part of a plasticizer composition for polymers, to plasticizer compositions comprising tripentyl esters of trimellitic acid, and to polymer compositions comprising tripentyl esters of trimellitic acid.

Discussion of the Background

Polyvinyl chloride (PVC) is one of the most economically important polymers. Both rigid PVC and flexible PVC find a variety of uses.

For production of PVC-based products, processability is improved and further use-relevant properties are adjusted by adding plasticizers to the PVC. Because of their advantageous properties, some of the most important plasticizers for PVC and vinyl chloride-containing copolymers are still compounds from the group of the phthalates, especially diethylhexyl phthalate (DEHP), diisononyl phthalate (DINP) and diisodecyl phthalate (DIDP). Because of discussions about possible toxic effects of this substance class, alternatives to phthalate-based plasticizers have been sought for many years.

A novel class of plasticizers, presented in the article "Vinyl Plasticizers form Trimellitic Anhydride" (Soc. Plastics Engrs. Techn. Papers. Volume 8, Issue Session 22, Pages Paper 1,1-9, Journal 1962), is that of triesters of trimellitic acid (trimellitates), and the properties of the methyl, ethyl, butyl, n-hexyl, isooctyl, 2-ethylhexyl, n-octyl, isodecyl, n-octyldecyl and dibutylbenzyl triesters of trimellitic acid are compared to the properties of other plasticizers such as dioctyl phthalate and diisooctyl phthalate. The studies presented in this article show that tributyl trimellitate has good processability, but the processability of the trimellitates decreases with increasing length of the alkyl radical.

Patent EP 354 700 B1 describes the suitability of mixtures of trimellitates having alkyl radicals with different carbon numbers, wherein at least 85 mol % of the alkyl radicals are linear, for powder forming of a PVC composition, but also states that some trimellitates are poorly adsorbed by PVC particles, i.e. have poor processability.

Good compatibility of mixed trimellitates of phenylpropanol and an alcohol having 4 to 10 carbon atoms with PVC and vinyl chloride-containing copolymers is disclosed by patent specification DE 23 48 511 C3. However, the phenylpropanol raw material is costly in terms of preparation and is additionally classified as an irritant to the skin and eyes.

Published specification WO 91/07459 A1 advocates the use of trimellitates, especially of tridecyl trimellitate, tridodecyl trimellitate, tri-n-octyl trimellitate and mixed $C_{8-10}$ trimellitates as plasticizers for styrene-acrylonitrile copolymers and explicitly advocates linear alkyl radicals.

Patent EP 479 260 B1 describes cellulose films which, as well as a phosphoric ester plasticizer, contain a trimellitate plasticizer, especially trimethyl or triethyl trimellitate.

The textbook "Plasticizers—Principles and Practice" by A. S. Wilson (The Institute of Materials, 1995, pages 166 to 170) ascribes good migration properties to the trimellitates, but classifies exclusively trimellitates with alcohol radicals containing 7 to 9 carbon atoms or mixtures of $C_6$ and $C_8$ esters or $C_7$, $C_8$ and $C_9$ esters of trimellitic acid as being of commercial interest, emphasizing tri-2-ethylhexyl trimellitate as being the most important trimellitate.

Published specification JP 2005/230058 A advocates improving the migration properties of tri-2-ethylhexyl trimellitate, which are inadequate for medical applications, by admixing with epoxidized vegetable oils.

SUMMARY OF THE INVENTION

It was an object of the present invention to provide plasticizers usable as a phthalate substitute. These plasticizers were to have processability with polymers, especially with PVC and vinyl chloride-containing copolymers, at least at the level of DINP and tri-2-ethylhexyl trimellitate and preferably even better. These plasticizers were preferably to have a low tendency to migrate out of plasticized PVC or plasticized vinyl chloride-containing copolymers into other materials.

This object is achieved by mixtures according to claim 1.

DETAILED DESCRIPTION OF THE INVENTION

The present invention provides mixtures of triisopentyl esters of trimellitic acid comprising isomeric pentyl radicals in which more than 5 mol % of the isomeric pentyl radicals incorporated in the ester mixture are branched.

The syllable "iso" indicates a mixture of two or more isomers having a carbon number in common, here having 5 carbon atoms. In accordance with the familiar definition of the term "mixture", mixtures according to the invention always include at least two different isomers of the tripentyl ester of trimellitic acid.

Corresponding mixtures are also referred to hereinafter as mixtures according to the invention or inventive mixtures of triisopentyl esters (of trimellitic acid).

It has been found that, surprisingly, mixtures according to the invention have better processability with PVC than DINP and tri-2-ethylhexyl trimellitate and at the same time have a very much lower tendency to migrate into non-plasticized PVC (rPVC) or into high-impact polystyrene (HIPS), which is lower than that of DINP, tri-n-butyl trimellitate, tri-n-pentyl trimellitate and tri-n-hexyl trimellitate. Moreover, plastisols or semi-finished products containing mixtures according to the invention have lower volatility than comparable plastisols or semi-finished products comprising DINP or tri-n-butyl trimellitate. Furthermore, the mixtures according to the invention can be processed at much lower temperatures or much more quickly at the same temperature than trimellitates containing six or more carbon atoms in the alkyl radical. Thus, the mixtures according to the invention have a unique combination of good processability, low migration tendency and low volatility.

Preference is given to mixtures according to the invention in which at least 15 mol %, preferably at least 20 mol %, preferably at least 25 mol %, more preferably at least 50 mol %, further preferably at least 67 mol %, even more preferably at least 75 mol % and especially at least 80 mol % of the isomeric pentyl radicals incorporated in the ester mixture are branched, since it has been shown that such mixtures exhibit a particularly low tendency to migrate into other polymers.

A branched pentyl radical is preferably a methylbutyl radical. Accordingly, preference is given to mixtures according to the invention in which the branched pentyl radicals consist of methylbutyl radicals to an extent of at least 50 mol %, preferably to an extent of at least 60 mol %, further preferably to an extent of at least 70 mol %, still further preferably to an extent of at least 80 mol %, even more preferably to an extent of at least 90 mol % and especially to an extent of at least 95 mol %.

It has likewise been found that the tendency to migrate is particularly low when the branched isomeric pentyl radicals have a high proportion of 2-methylbutyl radicals. In a preferred embodiment, therefore, at least 50 mol %, preferably at least 60 mol %, more preferably at least 70 mol %, further preferably at least 80 mol %, especially preferably at least 90 mol % and especially at least 95 mol % of the branched isomeric pentyl radicals incorporated in the ester mixture are 2-methylbutyl radicals.

In a particularly preferred embodiment, the mixture according to the invention consists to an extent of at least 75 mol % and especially to an extent of at least 90 mol % of esters containing 2-methylbutyl and/or linear pentyl radicals, where the molar ratio of 2-methylbutyl radicals to linear pentyl radicals within these esters is in the range from 5:95 to 80:20, preferably in the range from 10:90 to 75:25 and especially in the range from 20:80 or 30:70 to 70:30.

However, it may also be advantageous, especially when the maximum viscosity during the gelation of a plastisol containing a mixture according to the invention is to be kept particularly low, when the branched isomeric pentyl radicals consist in a high proportion of 3-methylbutyl radicals. In such a case, at least 10 mol %, preferably at least 20 mol %, more preferably at least 30 mol %, further preferably at least 40 mol %, with preference at least 50 mol %, preferably at least 60 mol %, further preferably at least 70 mol %, especially preferably at least 80 mol % and especially at least 90 mol % of the branched isomeric pentyl radicals incorporated in the ester mixture are 3-methylbutyl radicals. It may additionally be advantageous when the mixture according to the invention consists to an extent of at least 75 mol % and especially to an extent of at least 90 mol % of esters containing 3-methylbutyl and/or linear pentyl radicals, and at the same time the molar ratio of 3-methylbutyl radicals to linear pentyl radicals is 5:95 to 80:20, preferably in the range from 10:90 to 75:25 and especially in the range from 20:80 or 30:70 to 70:30.

It has further been found that the processability of the mixtures according to the invention and the efficiency of the mixtures according to the invention rise with increasing content of linear pentyl radicals. For this reason, it may be advantageous when more than 10 mol %, preferably more than 20 mol %, further preferably more than 30 mol %, more preferably more than 40 mol %, even more preferably more than 50 mol %, with further preference more than 60 mol %, preferably more than 70 mol % and especially more than 80 mol % of the isomeric pentyl radicals incorporated in the ester mixture are linear. Because of a reduced tendency to migrate, it may also be preferable that the proportion of linear pentyl radicals in the isomeric pentyl radicals incorporated in the ester mixture is less than 50 mol %, preferably less than 30 mol %, further preferably less than 10 mol % and especially less than 5 mol %.

Preferably, the isomeric pentyl radicals incorporated in the mixture of the triisopentyl esters of trimellitic acid are based on mixtures of primary pentanols, since these have higher efficiency and better processability than the corresponding triisopentyl esters based on secondary alcohols.

The present invention preferably provides a mixture of triisopentyl esters of trimellitic acid comprising isomeric pentyl radicals in which more than 5 mol %, preferably at least 15 mol %, especially at least 20 mol %, of the isomeric pentyl radicals incorporated in the ester mixture are branched and, at the same time, preferably at least 50 mol % and especially at least 90 mol % of the branched isomeric pentyl radicals incorporated in the ester mixture are 2-methylbutyl radicals.

Preferably, this mixture contains at least 67 mol % and especially at least 80 mol % of branched pentyl radicals based on all the isomeric pentyl radicals incorporated in the ester mixture.

The present invention preferably further provides a mixture of triisopentyl esters of trimellitic acid comprising isomeric pentyl radicals in which more than 5 mol % of the isomeric pentyl radicals incorporated in the ester mixture are branched and more than 20 mol %, preferably more than 50 mol % and especially more than 85 mol % of the isomeric pentyl radicals incorporated in the ester mixture are linear.

Preferably, at least 50 mol %, preferably at least 80 mol % and especially at least 95 mol % of the branched isomeric pentyl radicals incorporated here in the ester mixture are 2-methylbutyl radicals.

The present invention additionally provides the preparation process for the mixtures according to the invention and hence a process for preparing mixtures of triisopentyl esters of trimellitic acid comprising isomeric pentyl radicals, characterized in that trimellitic acid and/or a trimellitic acid derivative is/are reacted with a mixture of isomeric pentanols, more than 5 mol % of the isomeric pentyl radicals incorporated in the mixture of isomeric pentanols being branched.

Suitable trimellitic acid derivatives are trimellitic anhydride, acid halides of trimellitic acid and trimellitic triesters.

With preference, in this process, at least 15 mol %, preferably at least 20 mol %, more preferably at least 25 mol %, especially preferably at least 50 mol %, further preferably at least 67 mol %, even more preferably at least 75 mol % and especially at least 80 mol % of the isomeric pentyl radicals incorporated in the mixture of the isomeric pentanols are branched, where the branched pentyl radicals preferably consist to an extent of at least 80 mol % of methylbutyl radicals.

Particularly advantageous mixtures are obtained when, in the process, at least 50 mol %, preferably at least 60 mol %, more preferably at least 70 mol %, further preferably at least 80 mol %, especially preferably at least 90 mol % and especially at least 95 mol % of the branched isomeric pentyl radicals incorporated in the mixture of the isomeric pentanols are 2-methylbutyl radicals.

In some embodiments, it is preferable when, in the process, a mixture of isomeric pentanols in which more than 10 mol %, preferably more than 20 mol %, further preferably more than 30 mol %, more preferably more than 40 mol %, even more preferably more than 50 mol %, with further preference more than 60 mol %, preferably more than 70 mol % and especially more than 80 mol % of the isomeric pentyl radicals incorporated in the mixture of the isomeric pentanols are linear is used.

Preference is given to preparing the inventive mixtures of triisopentyl esters of trimellitic acid using the trimellitic acid derivative trimellitic anhydride.

If the mixtures according to the invention are prepared by transesterification, preferably one or more trialkyl trimellitates in which the alkyl radicals of the ester functions each comprise fewer than 4 carbon atoms is/are transesterified with a mixture of isomeric pentanols, more than 5 mol % of the isomeric pentyl radicals incorporated in the mixture of isomeric pentanols being branched.

Preference is given to transesterifying trimethyl trimellitate or triethyl trimellitate, especially trimethyl trimellitate, to give the inventive mixtures of triisopentyl esters of trimellitic acid.

The esterification or transesterification is preferably conducted in the presence of a catalyst or a plurality of catalysts, for example using Brønsted or Lewis acids or bases as catalyst. Particularly suitable catalysts have been found to be sulphuric acid, methanesulphonic acid, p-toluenesulphonic acid and metal compounds. Examples of particularly preferred catalysts are tin powder, tin(II) oxide, tin(II) oxalate, titanium catalysts such as tetraisopropyl orthotitanate, tetrabutyl orthotitanate or tetrapentyl orthotitanate, and also zirconium esters such as tetrabutyl zirconate or tetrapentyl zirconate. Examples of particularly preferred basic catalysts are alkoxides such as sodium methoxide and potassium methoxide.

In order to shift the equilibrium that develops in the reaction in favour of the mixtures according to the invention, it may be advantageous to distil the water that forms in the esterification or the alcohol that forms in the transesterification out of the reaction mixture. Preference is given to distilling off an azeotrope of water and alcohol. Because of possible foam formation, it is possible here to work with a column.

In addition, it may be advantageous to use the mixture of isomeric pentanols in an overall excess. Preference is given to using the mixture of isomeric pentanols in an excess of 5 to 50 mol %, especially 9 to 30 mol %, of the molar amount needed to form the inventive mixture of triisopentyl esters of trimellitic acid. With preference, the excess alcohol remaining after the reaction has ended is reused for a further esterification or transesterification or another chemical reaction. For this purpose, the excess alcohol can be worked up to increase its purity. For example, it is possible to at least partly condense an alcohol-water azeotrope that has been distilled off, to separate the condensate into an aqueous phase and an organic phase and to remove unwanted by-products—for example olefins formed by elimination of water from the alcohol—from the organic phase, before the organic phase that has then been purified is recycled into the reaction system or finds use for another reaction or for another purpose.

It is additionally possible to treat the reaction mixture from the esterification or transesterification with superheated alcohol vapour. In this way, it is possible to save a portion of the energy input through other media and to achieve good mixing of the reaction medium.

Other means of saving energy are to feed the mixture of isomeric pentanols into the reaction system at a temperature above ambient temperature, for example at 40° C. or 60° C. It is also possible to use trimellitic anhydride with elevated temperature, preferably in the form of a melt, in the process according to the invention. As well as the advantage of the energy input, this procedure additionally enables better mixing of the reaction medium and a reaction that proceeds more quickly.

In the case of preparation of inventive mixtures of triisopentyl esters of trimellitic acid from trimellitic acid, trimellitic anhydride or trialkyl trimellitates, especially from trimellitic anhydride, it is preferable to heat the reaction mixture to boiling and to add, with preference, at least 0.2 molar equivalent, preferably at least 0.25 molar equivalent and especially at least 0.3 molar equivalent of the amount of mixture of isomeric pentanols needed to introduce all the isomeric pentyl radicals incorporated in the ester mixture to the reaction mixture containing the trimellitic acid and/or the trimellitic acid derivative only after attainment of the boiling temperature. In the calculation of the amount of the mixture of isomeric pentanols which is added to the reaction mixture only after attainment of the boiling temperature, it should be ensured that any excess amounts of isomeric pentanols used are also added to the reaction mixture only after attainment of the boiling temperature. Such a reaction regime makes it possible to obtain higher yields of inventive mixture of triisopentyl esters of trimellitic acid within a shorter reaction time than is the case when the entire mixture of isomeric pentanols is available in contact with the trimellitic acid and/or with the trimellitic acid derivative prior to attainment of the boiling temperature.

After the esterification or transesterification reaction has ended, the particular reaction mixture is worked up in a customary manner.

For example, it is possible to treat the crude ester with an aqueous base at an elevated pressure at least as high as the vapour pressure of water at the prevailing temperature. This process regime makes it possible to obtain reaction mixtures of good filterability.

In the processes for preparing inventive mixtures of triisopentyl esters of trimellitic acid, preference is given to using mixtures of primary pentanols in order to obtain plasticizers having good processability and high plasticizer efficiency, and also low volatility.

Suitable mixtures of primary pentanols are preparable by means of hydroformylation of butenes and subsequent or simultaneous hydrogenation. It may be advantageous to fractionate the mixture of isomeric butenes before supplying it to the hydroformylation and hence enrich or deplete particular butene isomers, in order to obtain, after hydroformylation and hydrogenation, mixtures of isomeric pentanols of such an isomer distribution that makes it possible to prepare inventive mixtures of triisopentyl esters of trimellitic acid. For a detailed discussion of the control of the isomer distribution of pentanols, reference should be made to the corresponding passages in the application US 2007/0287781 A1.

Further alternative access routes to the mixtures according to the invention involve, for example, fractionating aldehydes prepared by means of a hydroformylation and in this way enriching or depleting particular aldehyde isomers, in order to obtain, after hydrogenation, mixtures of isomeric pentanols of such an isomer distribution that makes it possible to prepare inventive mixtures of triisopentyl esters of trimellitic acid. Alternatively, it is additionally possible to fractionate mixtures of isomeric pentanols and here too to enrich or deplete particular pentanol isomers.

Alternatively, it is further possible to prepare a mixture of isomeric pentanols by the mixing of isomerically pure pentanols and to use said mixture in an esterification or transesterification. It is also possible to blend mixtures of isomeric pentanols which possibly do not have the isomer distribution required to implement the present invention with mixtures of isomeric pentanols of another composition and/or with one or more isomerically pure pentanols, in order to obtain, after the esterification or transesterification, mixtures of triisopentyl esters of trimellitic acid having the required properties.

In addition, it is possible to prepare the mixtures according to the invention not by selectively mixing the mixtures of isomeric pentanols for use in an esterification or transesterification but by selectively blending isomers of the tripentyl ester of trimellitic acid.

Accordingly, the present invention provides a process for preparing mixtures of triisopentyl esters of trimellitic acid comprising isomeric pentyl radicals, in which at least two isomerically pure tripentyl esters of trimellitic acid which differ in terms of the isomerism of the pentyl radicals incorporated in the ester, at least two mixtures of triisopentyl esters of trimellitic acid comprising isomeric pentyl radicals which differ in the isomer distributions of the isomeric pentyl radicals incorporated in the ester mixture, or at least one isomerically pure tripentyl ester of trimellitic acid and at least one mixture of triisopentyl esters of trimellitic acid comprising isomeric pentyl radicals are mixed with one another, such that more than 5 mol %, preferably at least 15 mol %, more preferably at least 20 mol %, more preferably still at least 25 mol %, especially preferably at least 50 mol %, further preferably at least 67 mol %, even more preferably at least 75 mol % and especially at least 80 mol % of the isomeric pentyl radicals incorporated in the commixed ester mixture are branched.

The inventive mixtures of triisopentyl esters of trimellitic acid can be used as the sole plasticizer or as part of a plasticizer composition comprising several polymer-plasticizing components in plastics.

The present invention accordingly further provides for the use of inventive mixtures of triisopentyl esters of trimellitic acid comprising isomeric pentyl radicals as plasticizer, or as part of a plasticizer composition comprising at least one further polymer-plasticizing compound in addition to the mixtures of triisopentyl esters of trimellitic acid, for polymers.

Suitable polymers are preferably selected from the group formed by polyvinyl chloride (PVC), homo- or copolymers based on ethylene, propylene, butadiene, vinyl acetate, glycidyl acrylate, glycidyl methacrylate, ethyl acrylate, butyl acrylate or methacrylate with alkoxy radicals of branched or unbranched alcohols having one to ten carbon atom(s), acrylonitrile or cyclic olefins, chlorosulphonated polyethylene, polyvinylidene chloride (PVDC), polyacrylates, more particularly polymethylmethacrylate (PMMA), polyalkyl methacrylate (PAMA), polyureas, silylated polymers, fluoropolymers, especially polyvinylidene fluoride (PVDF), polytetrafluoroethylene (PTFE), polyvinyl acetate (PVAc), polyvinyl alcohol (PVA), polyvinyl acetals, especially polyvinyl butyral (PVB), polystyrene polymers, especially polystyrene (PS), expandable polystyrene (EPS), acrylonitrile-styrene-acrylate (ASA), styrene-acrylonitrile (SAN), acrylonitrile-butadiene-styrene (ABS), styrene-maleic anhydride copolymer (SMA), styrene-methacrylic acid copolymer, polyolefins, especially polyethylene (PE) or polypropylene (PP), thermoplastic polyolefins (TPO), polyethylene-vinyl acetate (EVA), polycarbonates, polyethylene terephthalate (PET), polybutylene terephthalate (PBT), polyoxymethylene (POM), polyamide (PA), polyethylene glycol (PEG), polyurethane (PU), thermoplastic polyurethane (TPU), polysulphides (PSu), biopolymers, especially polylactic acid (PLA), polyhydroxybutyral (PHB), polyhydroxyvaleric acid (PHV), polyesters, starch, cellulose and cellulose derivatives, especially nitrocellulose (NC), ethylcellulose (EC), cellulose acetate (CA), cellulose acetate/butyrate (CAB), rubber and silicones.

Preferred polymers are polyvinyl chloride, copolymers of vinyl chloride with vinyl acetate or with butyl acrylate, polyalkyl methacrylate (PAMA), polyvinyl butyral (PVB), chlorosulphonated polyethylene, polyurethane, polysulphides, polylactic acid (PLA), polyhydroxybutyral (PHB) and nitrocellulose.

Particular preference is given to the use of an ester mixture according to the invention as plasticizer or as part of a plasticizer composition for PVC or vinyl chloride-containing copolymers.

Preference is given to using the inventive mixtures of triisopentyl esters of trimellitic acid as plasticizer or as part of a plasticizer composition in adhesives, sealing compounds, coating materials, paints, inks, plastisols, foams, synthetic leather, floorcoverings (e.g. top layer), roofing membranes, underbody protection, fabric coatings, cables, wire insulation, hoses, extruded articles, films, in the automotive interior sector, in wallcoverings, liquid inks, toys, contact sheets, food packaging or medical articles, for example tubes or blood bags.

In a further embodiment, the inventive mixtures of triisopentyl esters are used as solvent for additives, for example as solvent for adhesion promoters.

As already mentioned above, the inventive mixtures of triisopentyl esters of trimellitic acid together with one or more further polymer-plasticizing compounds can form a plasticizer composition. According to the end use, one or more polymer-plasticizing compounds are blended with the inventive mixtures of the triisopentyl esters of trimellitic acid and so the properties of the resulting plasticizer composition are controlled. In a particularly preferred embodiment of a plasticizer composition according to the invention, said composition contains less than 5% by mass and especially less than 0.5% by mass and most preferably less than 0.1% by mass of phthalate-containing compounds. The further polymer-plasticizing compounds are preferably selected from the group of the adipates, benzoates, for example monobenzoates or glycol dibenzoates, chlorinated hydrocarbons, citrates, cyclohexanedicarboxylates, epoxidized fatty acid esters, epoxidized vegetable oils, epoxidized acylated glycerides, furandicarboxylates, phosphates, phthalates (preferably in very small amounts), succinates, sulphonamides, sulphonates, terephthalates, trimellitates or oligomeric or polymeric esters based on adipic, succinic or sebacic acid.

The present invention also provides a plasticizer composition comprising inventive mixtures of triisopentyl esters of trimellitic acid comprising isomeric pentyl radicals and at least one further polymer-plasticizing compound from the group of the alkyl benzoates, dialkyl adipates, glycerol esters, trialkyl citrates, acylated trialkyl citrates, glycol dibenzoates, trimellitates with radicals other than those described in the present invention, dialkyl terephthalates, dialkyl phthalates, esters of furandicarboxylic acid, dialkanoyl esters of dianhydrohexitols (e.g. isosorbide), epoxidized fatty acid alkyl esters, polymer plasticizers, for example the polyadipates, and dialkyl esters of cyclohexane-1,2-, -1,3- or -1,4-dicarboxylic acid.

The present invention preferably provides a plasticizer composition comprising inventive mixtures of triisopentyl esters of trimellitic acid comprising isomeric pentyl radicals and diisononyl terephthalate (DINT). Corresponding plasticizer compositions are notable for low volatility. These plasticizer compositions are usable in a particularly advantageous manner for high-temperature applications such as cables, since products comprising corresponding plasticizer compositions have good heat resistance.

The present invention preferably further provides a plasticizer composition comprising inventive mixtures of triisopentyl esters of trimellitic acid comprising isomeric pentyl radicals and 1,2- or 1,4-cyclohexanedicarboxylic esters, especially diisononyl esters. Products comprising these plasticizer compositions are particularly notable in that they have improved cold flexibility. Moreover, plastisols comprising corresponding plasticizer compositions have better processability because of a lowered viscosity.

The present invention preferably further provides a plasticizer composition comprising inventive mixtures of triisopentyl esters of trimellitic acid comprising isomeric pentyl radicals and epoxidized fatty acid alkyl esters having a chain length of the alkyl radicals of 4 to 6 carbon atoms. Plastisols comprising corresponding plasticizer compositions have good processability because of a lowered viscosity and good gelation.

Preference is likewise given to a plasticizer composition comprising inventive mixtures of triisopentyl esters of trimellitic acid comprising isomeric pentyl radicals and trialkyl esters of trimellitic acid in which the alkyl radicals contain 6 or more, preferably 7, 8, 9, 10 or 11, carbon atoms. Preference is also given to plasticizer compositions comprising inventive mixtures of triisopentyl esters of trimellitic acid comprising isomeric pentyl radicals and polymer plasticizers. The embodiments of the inventive plasticizer compositions or of the products produced therefrom that are cited in this paragraph have particularly low volatility.

The present invention further provides a polymer composition comprising an inventive mixture of triisopentyl esters of trimellitic acid or a plasticizer composition of the invention and one or more polymers from the group formed by polyvinyl chloride, copolymers of vinyl chloride with vinyl acetate or with butyl acrylate, polyalkyl methacrylate (PAMA), polyvinyl butyral (PVB), polyurethane, polysulphides, polylactic acid (PLA), polyhydroxybutyral (PHB) and nitrocellulose.

Based on 100 parts by mass of polymer, preferred polymer compositions comprise from 5 to 200, preferably from 10 to 150, parts by mass of plasticizer.

Preference is given to the use of the mixture of the invention as plasticizer or as part of a plasticizer composition for polyvinyl chloride, and particular preference is accordingly given to the polymer compositions comprising the ester mixture of the invention and PVC and/or vinyl chloride-containing copolymers.

The polymer is preferably a suspension PVC, bulk PVC, microsuspension PVC or emulsion PVC.

In one embodiment, the polymer composition of the invention comprises, aside from the inventive mixture of triisopentyl esters of trimellitic acid, less than 50% by mass, less than 20% by mass, less than 10% by mass or no further polymer-plasticizing compounds, where the percentages by mass are based on the total mass of the polymer composition.

Polymer compositions according to the invention preferably comprise not only the polymer or a mixture of two or more polymers and the inventive mixture of triisopentyl esters of trimellitic acid and one or more further optional polymer-plasticizing compounds but also one or more additives from the group of the heat stabilizers, fillers, pigments, blowing agents, biocides, UV stabilizers, light stabilizers, costabilizers, antioxidants, viscosity regulators, deaerating agents, adhesion promoters, lubricants and colourants.

Preferably, polymer compositions of the invention comprise viscosity regulators, which are advantageously used in order to lower the viscosity of plastisols comprising mixtures according to the invention.

The polymer compositions according to the invention can be used in adhesives, sealing compounds, coating materials, paints, inks, plastisols, foams, synthetic leather, floorcoverings (e.g. top layer), roofing membranes, underbody protection, fabric coatings, cables, wire insulation, hoses, extruded articles, films, in the automotive interior sector, in wallcoverings, liquid inks, toys, contact sheets, food packaging or medical articles, for example tubes or blood bags.

As well as the mixtures of triisopentyl esters of trimellitic acid with a given isomer distribution, which are referred to in this text simply as mixtures according to the invention, and the preparation and use thereof, the present invention additionally extends to the use of tripentyl esters of trimellitic acid as plasticizers, to the applications resulting therefrom and to an improved preparation process for these esters.

The present invention accordingly provides a process for preparing tripentyl esters of trimellitic acid, in which trimellitic acid and/or a trimellitic acid derivative is/are reacted with pentanol, wherein the reaction mixture is heated to boiling and at least 0.2 molar equivalent, preferably at least 0.25 molar equivalent and especially at least 0.3 molar equivalent of the amount of pentanol needed to introduce all the pentyl radicals incorporated in the ester mixture is added to the reaction mixture containing the trimellitic acid and/or the trimellitic acid derivative only after attainment of the boiling temperature. In the calculation of the amount of pentanol which is added to the reaction mixture only after attainment of the boiling temperature, it should be ensured that any excess amounts of pentanol used are also added to the reaction mixture only after attainment of the boiling temperature. Such a reaction regime makes it possible to obtain higher yields of tripentyl esters of trimellitic acid within a shorter reaction time than is the case when all the pentanol is available in contact with the trimellitic acid and/or with the trimellitic acid derivative prior to attainment of the boiling temperature.

Suitable trimellitic acid derivatives are trimellitic anhydride, acid halides of trimellitic acid and trimellitic triesters.

In this process, preference is given to using the trimellitic acid derivative trimellitic anhydride and esterifying the latter with pentanol.

In an alternative embodiment, the tripentyl esters of trimellitic acid are prepared from a trialkyl trimellitate by means of transesterification. In this case, the alkyl radicals of the ester functions each preferably comprise fewer than 4 carbon atoms.

The esterification or transesterification is preferably conducted in the presence of a catalyst or a plurality of catalysts, for example using Brønsted or Lewis acids or bases as catalyst. Particularly suitable catalysts have been found to be sulphuric acid, methanesulphonic acid, p-toluenesulphonic acid and metal compounds. Examples of particularly preferred catalysts are tin powder, tin(II) oxide, tin(II) oxalate, titanium catalysts such as tetraisopropyl orthotitanate, tetrabutyl orthotitanate or tetrapentyl orthotitanate, and also zirconium esters such as tetrabutyl zirconate or tetrapentyl zirconate. Examples of particularly preferred basic catalysts are alkoxides such as sodium methoxide and potassium methoxide.

In order to shift the equilibrium that develops in the reaction in favour of the tripentyl esters, it may be advantageous to distil the water that forms in the esterification or the alcohol that forms in the transesterification out of the reaction mixture. Because of possible foam formation, it is possible here to work with a column. In addition, it may be advantageous to use the pentanol in an overall excess. Preference is given to using the pentanol in an excess of 5 to 50 mol %, especially 9 to 30 mol %, of the molar amount needed to form the tripentyl esters of trimellitic acid. After the esterification or transesterification reaction has ended, the particular reaction mixture is worked up in a customary manner.

In the process described here for preparation of tripentyl esters of trimellitic acid, preference is also given to using mixtures of primary pentanols in order to obtain plasticizers having good processability and high plasticizer efficiency, and also low volatility.

Preferably, more than 10 mol %, preferably more than 20 mol %, further preferably more than 30 mol %, especially preferably more than 40 mol %, very especially preferably more than 50 mol %, with preference more than 60 mol %, preferably more than 70 mol %, more preferably still more than 80 mol % and especially more than 90 mol % of the pentyl radicals present in the tripentyl trimellitate mixture prepared or in the pentanol used are linear. With particular preference, n-pentanol is used and tri-n-pentyl trimellitate is prepared.

The tripentyl esters of trimellitic acid can be used as the sole plasticizer or as part of a plasticizer composition comprising several polymer-plasticizing components in plastics.

The present invention accordingly further provides for the use of tripentyl esters of trimellitic acid as plasticizer, or as part of a plasticizer composition comprising at least one further polymer-plasticizing compound in addition to the tripentyl ester(s) of trimellitic acid, for polymers, especially for PVC or vinyl chloride-containing copolymers. In this context, preference is given especially to the tri-n-pentyl ester of trimellitic acid because of its very good processability and the very good Shore A hardness of test specimens containing the tri-n-pentyl ester of trimellitic acid, and hence because of its very good efficiency.

Preferred polymers are polyvinyl chloride, copolymers of vinyl chloride with vinyl acetate or with butyl acrylate, polyalkyl methacrylate (PAMA), polyvinyl butyral (PVB), chlorosulphonated polyethylene, polyurethane, polysulphides, polylactic acid (PLA), polyhydroxybutyral (PHB) and nitrocellulose.

Preference is given to using the tripentyl esters of trimellitic acid as plasticizer or as part of a plasticizer composition in adhesives, sealants, coating materials, paints, inks, plastisols, foams, synthetic leather, floorcoverings (e.g. top layer), roofing membranes, underbody protection, fabric coatings, cables, wire insulation, hoses, extruded articles, films, in the automotive interior sector, in wallcoverings, liquid inks, toys, contact sheets, food packaging or medical articles, for example tubes or blood bags. In a further embodiment, the tripentyl esters of trimellitic acid are used as solvent for additives, for example as solvent for adhesion promoters.

The tripentyl esters of trimellitic acid together with one or more further polymer-plasticizing compounds can form a plasticizer composition. According to the end use, one or more polymer-plasticizing compounds are blended with the tripentyl esters of trimellitic acid and so the properties of the resulting plasticizer composition are controlled. In a particularly preferred embodiment of a plasticizer composition according to the invention, said composition contains less than 5% by mass and especially less than 0.5% by mass of phthalate-containing compounds. The further polymer-plasticizing compounds are preferably selected from the group of the adipates, benzoates, for example monobenzoates or glycol dibenzoates, chlorinated hydrocarbons, citrates, cyclohexanedicarboxylates, epoxidized fatty acid esters, epoxidized vegetable oils, epoxidized acylated glycerides, furandicarboxylates, phosphates, phthalates (preferably in very small amounts), succinates, sulphonamides, sulphonates, terephthalates, trimellitates or oligomeric or polymeric esters based on adipic, succinic or sebacic acid.

The present invention also provides a plasticizer composition comprising one or more tripentyl esters of trimellitic acid and at least one further polymer-plasticizing compound from the group of the alkyl benzoates, dialkyl adipates, glycerol esters, trialkyl citrates, acylated trialkyl citrates, glycol dibenzoates, trimellitates with radicals other than those described in the present invention, dialkyl terephthalates, dialkyl phthalates, esters of furandicarboxylic acid, dialkanoyl esters of dianhydrohexitols (e.g. isosorbide), epoxidized fatty acid alkyl esters, polymer plasticizers, for example the polyadipates, and dialkyl esters of cyclohexane-1,2-, -1,3- or -1,4-dicarboxylic acid.

The present invention further provides a polymer composition comprising tripentyl esters of trimellitic acid or a plasticizer composition comprising tripentyl esters of trimellitic acid and one or more polymers from the group formed by polyvinyl chloride, copolymers of vinyl chloride with vinyl acetate or with butyl acrylate, polyalkyl methacrylate (PAMA), polyvinyl butyral (PVB), polyurethane, polysulphides, polylactic acid (PLA), polyhydroxybutyral (PHB) and nitrocellulose.

Based on 100 parts by mass of polymer, preferred polymer compositions comprise from 5 to 200, preferably from 10 to 150, parts by mass of plasticizer.

Preference is given to the use of tripentyl esters of trimellitic acid as plasticizer or as part of a plasticizer composition for polyvinyl chloride, and particular preference is accordingly given to polymer compositions comprising tripentyl esters of trimellitic acid and PVC and/or vinyl chloride-containing copolymers. The polymer is preferably a suspension PVC, bulk PVC, microsuspension PVC or emulsion PVC.

Preferred polymer compositions preferably comprise not only the polymer or a mixture of two or more polymers and tripentyl esters of trimellitic acid and one or more further optional polymer-plasticizing compounds but also one or more additives from the group of the heat stabilizers, fillers, pigments, blowing agents, biocides, UV stabilizers, light stabilizers, costabilizers, antioxidants, viscosity regulators, deaerating agents, adhesion promoters, lubricants and colourants.

Preferably, polymer compositions of the invention comprise viscosity regulators, which are advantageously used in order to lower the viscosity of plastisols comprising mixtures according to the invention.

The polymer compositions according to the invention can be used in adhesives, sealants, coating materials, paints, inks, plastisols, foams, synthetic leather, floorcoverings (e.g. top layer), roofing membranes, underbody protection, fabric coatings, cables, wire insulation, hoses, extruded articles, films, in the automotive interior sector, in wallcoverings, liquid inks, toys, contact sheets, food packaging or medical articles, for example tubes or blood bags.

As well as the mixtures of tripentyl esters of trimellitic acid, which are referred to in simplified form in this text as mixtures according to the invention, and preparation and use thereof as plasticizers or as part of a plasticizer composition for polymers, plasticizer compositions comprising tripentyl esters of trimellitic acid and polymer compositions comprising tripentyl esters of trimellitic acid, the present invention additionally extends to tripentyl cyclohexane-1,2,4-tricarboxylates and isomer mixtures thereof, which are referred to in accordance with the nomenclature introduced above as triisopentyl cyclohexane-1,2,4-tricarboxylates. These esters or ester mixtures are preparable, for example, by ring hydrogenation of the corresponding tripentyl esters/tripentyl ester mixtures. Suitable processes for hydrogenation are described, for example, in US 2015/0246867 A1, U.S. Pat. No. 6,284,917 B1 or U.S. Pat. No. 7,361,714 B2. Alternatively, these esters/ester mixtures can also be obtained by an esterification of cyclohexane-1,2,4-tricarboxylic acid or suitable derivatives (e.g. anhydride, acid chloride) or by transesterification of an analogous ester (for example by transesterification of trimethyl cyclohexane-1,2,4-tricarboxylate).

The present invention accordingly also provides tripentyl cyclohexane-1,2,4-tricarboxylates which have preferably been prepared by ring hydrogenation of tripentyl esters of trimellitic acid, by esterification of cyclohexane-1,2,4-tricarboxylic acid or a cyclohexane-1,2,4-tricarboxylic acid derivative, or by transesterification of a cyclohexane-1,2,4-tricarboxylic triester of low molecular weight, with pentanol in each case. The present invention accordingly also provides triisopentyl cyclohexane-1,2,4-tricarboxylates which have preferably been prepared by ring hydrogenation of triisopentyl esters of trimellitic acid, by esterification of cyclohexane-1,2,4-tricarboxylic acid or a cyclohexane-1,2,4-tricarboxylic acid derivative or by transesterification of a cyclohexane-1,2,4-tricarboxylic triester of low molecular weight, with isopentanol in each case.

Compared to the analogous tripentyl esters of trimellitic acid with equal isomer distribution of the pentyl groups, these cyclohexane-1,2,4-tricarboxylic esters are notable for a much lower viscosity (as pure product and in PVC plastisol formulations), elevated plasticizer efficiency and elevated UV stability in PVC films. Compared to the longer-chain cyclohexane-1,2,4-tricarboxylic esters (e.g. tri-2-ethylhexyl cyclohexane-1,2,4-tricarboxylate, triisononyl cyclohexane-1,2,4-tricarboxylate), the tripentyl esters and triisopentyl esters are found to be superior, for example, in terms of gelation and efficiency.

Accordingly, the present invention further provides for the use of the tripentyl cyclohexane-1,2,4-tricarboxylates and of the triisopentyl cyclohexane-1,2,4-tricarboxylate isomer mixture as plasticizer or as part of a plasticizer composition, comprising, in addition to the tri(iso)pentyl cyclohexane-1,2,4-tricarboxylate(s), at least one further polymer-plasticizing compound, for polymers, especially for PVC or vinyl chloride-containing copolymers.

The present invention further provides plasticizer compositions and polymer compositions comprising tri(iso)pentyl cyclohexane-1,2,4-tricarboxylate(s).

Having generally described this invention, a further understanding can be obtained by reference to certain specific examples which are provided herein for purposes of illustration only, and are not intended to be limiting unless otherwise specified.

EXAMPLES

Examples 1 to 7: Preparation of Trimellitates by Esterification of Trimellitic Anhydride 576.0 g (3 mol) of trimellitic anhydride (Sigma Aldrich, 97% purity) and the amount $m_1$ of the alcohol A were introduced into an apparatus comprising a stirred flask with a stirrer, sampling stub, dropping funnel, immersed tube, thermometer and water separator with an attached jacketed coil condenser, with a 20 cm Raschig ring column upstream of the water separator in the case of the preparation of $C_4$ trimellitate. The apparatus was purged with nitrogen (6 l/h) through the immersed tube for one hour, before 0.8 g (0.75 mmol) of tetra-n-butyl titanate (Sigma Aldrich, >97% purity) was added. While sparging with nitrogen (6 l/h), which lasts until the end of the reaction, the mixture was heated to boiling while stirring. Water obtained as a result of the reaction was removed continuously by means of a water separator. From attainment of a reaction temperature of 240° C., the amount $m_2$ of the alcohol A and 0.8 g (0.75 mmol) of tetra-n-butyl titanate were metered in at such a rate that the reaction temperature did not fall below 240° C. As soon as 108 ml (6 mol) of water had been removed by means of the water separator, the acid number was determined on a sample of the reaction solution in accordance with DIN EN ISO 2114. Depending on the particular acid number determined, the reaction mixture was heated further until the acid number of the reaction mixture was below 0.1 mg KOH per g of sample (total reaction time t).

The cooled reaction mixture from the esterification was transferred into a stirred flask with stirrer, thermometer, immersed tube, Claisen distillation apparatus and receiver flask, and purged with nitrogen through the immersed tube for at least one hour, and then the pressure was reduced to about 1 mbar. The temperature was increased gradually up to 160° C. and the excess alcohol was distilled off. The mixture was cooled down under vacuum with introduction of nitrogen (20 mbar). On attainment of a temperature of 80° C., the pressure was equalized with nitrogen, and the crude product was admixed with 15 mmol of demineralized water and 0.5% by mass of activated carbon (Cabot Norit Nederland B.V., CAP Super, amount based on the reaction product assuming a yield of 100%) and stirred with introduction of nitrogen (6 l/h) at 80° C. for 15 minutes. Subsequently, the reaction mixture was heated to 160° C. under reduced pressure with introduction of nitrogen (20 mbar) for 2 hours and the last volatile components were removed. After cooling again down to 80° C., the reaction mixture, while sparging with nitrogen (6 l/h), was mixed with 2% by weight of basic alumina (Sigma Aldrich, Brockmann 1 type, amount based on the reaction product assuming a yield of 100%) and stirred at 80° C. for 1 hour.

The reaction mixture was then filtered at 80° C. through a Buchner funnel with filter paper and precompacted filtercake of filtration aid (D14 Perlite ex Knauf) into a suction bottle by means of reduced pressure. The filtrate was analysed by means of GC analysis with regard to purity and by means of NMR with regard to composition.

GC Analyses:

The GC analysis took place with the following parameters:
Capillary column: 30 m DB5; 0.25 mm ID; 0.25 µm film
Carrier gas: Helium
Column pressure: 150 kPa
Cool on-column injection
Oven temperature programme (duration: 51 min): 50° C. (for 1 min), heating at 15° C./min to 350° C. (hold temperature for 14 min)
Injector: 50° C.
Detector (FID): 425° C.
Injection volume: 0.3 µl Components in the sample chromatogram were identified using a comparative solution of the relevant esters. This was followed by standardization of the signals in the sample chromatogram to 100 area %. The molar ratios were determined in sufficient approximation from the area ratios of the individual signals.

The purity was determined via the fraction of the product signals as a proportion of the total areas in the chromatogram.

As an alternative to the NMR method described below, the nature and number of the isomeric pentyl radicals present in the triisopentyl esters can be determined by hydrolysis of the ester mixture in basic solution and subsequent GC analysis of the resulting alcohol mixture. It should be noted here that the GC conditions (especially column material and column dimensions, and temperature programme) permit separation of the alcohols into the individual isomers. Components in the sample chromatogram are then identified using a comparative solution of the relevant esters. This is followed by standardization of the signals in the sample chromatogram to 100 area %, such that it is possible to determine the molar ratios in sufficient approximation from the area ratios of the individual signals.

NMR Analyses:

The composition of the triisopentyl esters mixtures, i.e. the respective proportion of the different isomeric pentyl radicals in the totality of all pentyl radicals, can be ascertained, for example, by $^1$H NMR and $^{13}$C NMR spectroscopy. The determination of the composition was conducted here with the aid of $^1$H NMR spectroscopy on a solution of the triisopentyl esters mixture in deuterochloroform ($CDCl_3$). For the recording of the spectra, 20 mg of substance are dissolved in 0.6 ml of $CDCl_3$ (containing 1% by mass of TMS) and transferred to an NMR tube having a diameter of 5 mm. Both the substance to be analysed and the $CDCl_3$ used were first dried by means of molecular sieve in order to rule out distortion of the measurements by any water present. The NMR spectroscopy studies can in principle be conducted with any commercial NMR instrument. For the present NMR spectroscopy studies, an instrument of the Bruker Avance 500 type was used. The spectra were recorded at a temperature of 303 K with a delay of d1=5 seconds, 32 scans, a pulse length of about 9.5 µs (90° excitation pulse) and a sweep width of 10 000 Hz with a 5 mm BBO (broad band observer) sample head. The resonance signals were recorded relative to the chemical shift of tetramethylsilane (TMS=0 ppm) as internal standard. Other commercial NMR instruments give comparable results with the same operating parameters.

BRIEF DESCRIPTION OF THE DRAWINGS

FIG. 1 below is intended to serve for comprehension of the determination method elucidated. Of relevance here is the assigned numbering of the carbon atoms of the methyl groups and the methylene groups adjacent to the oxygen atom in an n-pentyl radical ($C^{14}H_3$ and $C^{10}H_2$), in a 2-methylbutyl radical ($C^{22}H_3$, $C^{23}H_3$ and $C^{19}H_2$) and in a 3-methylbutyl radical ($C^{18}H_3$, $C^{18'}H_3$ and $C^{15}H_2$).

Figure 1:
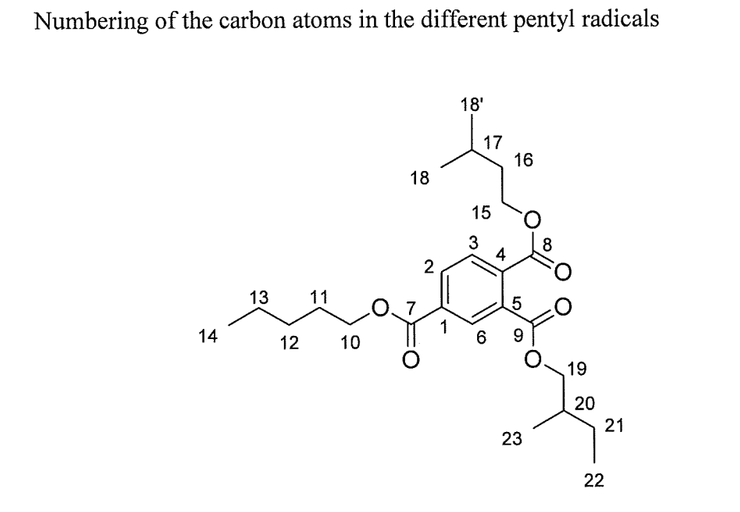

The resultant $^1$H NMR spectra of the mixtures of triisopentyl esters of trimellitic acid have, in the range from 0.5 ppm up to the minimum of the lowest valley in the range from 0.7 to 1.2 ppm, resonance signals which are formed by the signals of the hydrogen atoms of the methyl group(s) of the isomeric pentyl substituents ($C^{14}H_3$, $C^{18}H_3$, $C^{18'}H_3$, $C^{22}H_3$, $C^{23}H_3$). The signals in the range of chemical shifts from 3.60 to 4.55 ppm can be assigned essentially to the hydrogen atoms of the methylene group adjacent to the oxygen in the alcohol radical ($C^{10}H_2$, $C^{15}H_2$, $C^{19}H_2$). In this context, the protons on C19 are subject to a high-field shift because of the adjacent tertiary carbon atom and appear between 3.95 and 4.29 ppm, while the protons on C10 and C15 give signals at lower shifts of 4.29 to 4.55 ppm.

Quantification is effected by comparative determination of the area beneath the respective resonance signals, i.e. the area enclosed by the signal from the baseline. Commercial NMR software has program functions for integration of the signal area. In the present NMR spectroscopy study, the integration was conducted with the aid of the TopSpin® software, Version 3.1.

To determine the mean degree of branching of the isomeric pentyl radicals in the mixture according to the invention, the integral value of the signals in the range from 0.68 to 1.18 ppm ($I(CH_3)$) is first divided by the integral value of the signals in the range from 3.95 to 4.55 ppm ($I(OCH_2)$). In this way, an intensity ratio which states the ratio of the number of hydrogen atoms present in a methyl group to the number of hydrogen atoms present in a methylene group adjacent to an oxygen is obtained. Since three hydrogen atoms per methyl group and two hydrogen atoms in every methylene group adjacent to an oxygen are present, the intensities have to be divided by 3 and 2 respectively, in order to obtain the ratio of the number of methyl groups to the number of methylene groups adjacent to an oxygen in the pentyl radical. Since a linear n-pentyl radical having only one methyl group and one methylene group adjacent to an oxygen does not contain any branch and accordingly has to have a degree of branching of 0, it is necessary to subtract the quantity of 1 from the ratio.

The mean degree of branching DB can thus be calculated by the formula $$DB=2/3*I(CH_3)/I(OCH_2)-1$$

from the intensity ratio measured. In this formula, DB means mean degree of branching, $I(CH_3)$ means area integral assigned to the methyl hydrogen atoms, and $I(OCH_2)$ means area integral of the methylene hydrogen atoms adjacent to the oxygen.

The product may contain 2-methylbutyl radicals and 3-methylbutyl radicals each having a degree of branching of 1, and also n-pentyl radicals having a degree of branching of 0, which means that the maximum mean degree of branching of any triisopentyl ester is always 1. From the deviation of the mean degree of branching from the value of 1, it is therefore possible to determine the molar proportion of n-pentyl radicals ($x_{pentyl}$) in the molecule.

$$x_{pentyl}=1-DB$$

The proportion of 2-methylbutyl radicals can be calculated with the aid of the integration of the baseline-separated signals in the range from 3.95 to 4.55 ppm. Here too, the signals of the protons on C19 ($C^{19}H_2$; multiplet between 3.95 and 4.28 ppm) are separated from the signals of the protons on C10 and C15 ($C^{10}H_2$ and $C^{15}H_2$; multiplet between 4.29 and 4.55 ppm) in the minimum of the valley cut between the signal groups.

The molar proportion of 2-methylbutyl radicals ($x_{2-methylbutyl}$) can be calculated by the formula $$x_{2-methylbutyl}=I(OC^{19}H_2)/I(OCH_2)$$

by forming the ratio of the intensity of the signals for the $OC^{19}H_2$ protons ($I(OC^{19}H_2)$) to the intensity of all $OCH_2$ protons ($I(OCH_2)$).

The molar proportion of 3-methylbutyl radicals ($x_{3-methylbutyl}$) is thus calculated from the difference between the two previous molar proportions and 1.

$$x_{3-methylbutyl}=1-x_{2-methylbutyl}-x_{pentyl}$$

TABLE 1

Preparation of trimellitates by esterification of trimellitic anhydride

| Ex. | Alcohol A [molar ratio] | $m_1(A)$ [g] | $m_2(A)$ [g] | Reaction time t [h] | Purity by GC [%] | Composition: proportion of radicals in the ester mixture [molar ratio] |
|---|---|---|---|---|---|---|
| 1 | n-butanol | 416.9 | 352.1 | 5 | 97.8 | n-butyl |
| 2 | n-pentanol | 497.4 | 497.4 | 9 | 99.2 | n-pentyl |
| 3 | n-hexanol | 574.8 | 574.8 | 2.5 | 98.0 | n-hexyl |
| 4* | 2-methylbutanol/ n-pentanol 1:4 | 495.8 | 495.8 | 8.5 | 99.3 | 2-methylbutyl/ n-pentyl 0.20:0.80 |
| 5* | 2-methylbutanol/ n-pentanol 1:1 | 396.7 | 471.0 | 8 | 98.8 | 2-methylbutyl/ n-pentyl 0.50:0.50 |
| 6* | 2-methylbutanol/ 3-methylbutanol/ n-pentanol 1:1:1 | 495.8 | 495.8 | 7 | 98.9 | 2-methylbutyl/ 3-methylbutyl/ n-pentyl 0.33:0.33:0.34 |
| 7* | 2-methylbutanol/ n-pentanol 4:1 | 495.8 | 495.8 | 8 | 99.0 | 2-methylbutyl/ n-pentyl 0.79:0.21 |

*inventive

Example 8: Production of Dryblends, Rolled Sheets and Pressed Plaques

The test specimens required for the examples which follow are produced by dry mixing (dryblend production), calendering (rolling) and pressing of the following formulations:

TABLE 2

Dryblend formulation

| | phr |
|---|---|
| PVC (Solvin S271 PC; from Solvay) | 100 |
| Ester or ester mixture from Example 1, 2, 3, 4*, 5*, 6*, 7*, Tri-2-ethylhexyl trimellitate or DINP | 67 |
| Co-stabilizer-epoxidized soya bean oil (Drapex 39 ex Galata) | 3 |
| Thermal stabilizer based on Ba/Zn (Mark BZ 965 ex Galata) | 2 |
| Processing aid-fatty acid salts (Mark CD 41-0137 ex Galata) | 0.4 | phr: parts per hundred parts resin
Tri-2-ethylhexyl trimellitate: trioctyl trimellitate ex Sigma Aldrich, purity 99%
DINP: Vestinol 9 ex Evonik Industries, purity >99%

With dry mixtures, which are referred to as dryblends, it is possible, for example, after thermoplastic processing (e.g. calendering or extrusion) to produce cable and wire insulation, hoses or floors and roofing membranes.

The dryblends were produced in a Brabender planetary mixer. A thermostat (Lauda RC6) ensured temperature control of the mixing vessel in the planetary mixer. A PC recorded the data sent by the mixer.

The "Winmix" software was used to set the following parameters in the Brabender planetary mixer:

| | |
|---|---|
| Speed program: | active |
| Profile: | speed 50 rpm; hold time: 9 min; rise time (of speed): 1 min; speed 100 rpm; hold time: 20 min |
| Temperature: | 88° C. |
| Measurement range: | 2 Nm |
| Damping: | 3 |

The temperature in the mixing vessel was 88° C. after the one-hour equilibration period. Once the planetary mixer had conducted an internal calibration, the solid constituents (PVC, stabilizer), which had been weighed out beforehand in four times the amount (four times the amount in g based on Table 2 in phr) into a PE cup on a balance (Mettler XS6002S), were fed to the mixing vessel via a solids funnel and the filling stub present in the Brabender mixing vessel. The program was started and the powder mixture was stirred and equilibrated in the mixing vessel for 10 minutes, before the liquid constituents, which had likewise been weighed out in four times the amount in a PE cup on the balance, were fed in via a liquid funnel and the filling stub present in the Brabender mixing vessel. The mixture was stirred in a planetary mixer for a further 20 minutes. After the program had ended, the finished dry mixture (dryblend) was removed.

These dryblends were used to produce rolled sheets. The rolled sheets were produced on a Collin W150 AP calender. The Collin calender has an automatic sample turner and its temperature is controlled by means of an additional oil thermostat (Single STO 1-6-12-DM). Control was effected by means of Collin software.

A five-stage program was used to produce the rolled sheet:

| Stage | Designation | Temp. [° C.] | Duration [s] | Gap width [mm] | Speed [rpm] |
|---|---|---|---|---|---|
| 1 | Plastification of the dryblend | 165 | 60 | 0.2 | 5 |
| 2 | Increasing the gap size | 165 | 30 | 0.5 | 20 |
| 3 | Activation of the sample turner | 165 | 170 | 0.5 | 20 |
| 4 | Rolled sheet optimization | 165 | 30 | 0.5 | 25 |
| 5 | Rolled sheet removal | 165 | 60 | 0.5 | 7 |

On attainment of the roll temperature, the roll gap was calibrated. To start the measurement, the roll gap was adjusted to 0.2 mm. 160 g of each dryblend were weighed in and introduced into the roll gap with the rollers stationary. The program was started. The rollers started with a circumferential speed of 5 rpm and a friction of 20%. After about 1 min, the plastification was complete for the most part, and the roll gap was increased to 0.5 mm. Homogenization was effected 6 times by means of the automatic turning unit in the calender. After about 6 min, the rolled sheet was removed from the roller and cooled.

The pressed plaques were produced with a Collin laboratory press. The prefabricated rolled sheets (see above) were used to produce the pressed plaques. The lateral edges of the rolled sheets were removed with the aid of a cutting machine, then the rolled sheet was cut into pieces of about 14.5×14.5 cm in size. For pressed plaques of thickness 1 mm, 2 rolled sheet pieces in each case were placed one on top of the other into the stainless steel pressing frame of size 15×15 cm.

A three-stage program was used to produce the pressed plaques:

| Stage | Designation | Temp. [° C.] | Pressure [bar] | Duration [s] |
|---|---|---|---|---|
| 1 | Initial pressing | 175 | 5 | 60 |
| 2 | Pressing | 175 | 200 | 120 |
| 3 | Cooling | 40 | 200 | 270 |

The excess compression lip was removed after the press plaques had been produced.

Example 9: Plasticizer Absorption in the Dryblend

During the production of each dryblend, the rate of plasticizer absorption was determined, which serves as a measure of processability. A short plasticizer absorption time results in practice in low processing temperatures or elevated product throughput in an existing system.

The degree of plasticizer absorption was determined via the torque of the mixer as a function of time in the course of dryblend production.

For this purpose, by means of the hard- and software described in Example 8 for the dryblend production, the torque of the mixer was plotted against time. The torque rose to a maximum value from the addition of plasticizer or the plasticizer composition and dropped again from this, in order finally to attain a constant value or to drop further only minimally from what is called the dry point.

The period of time between the addition of the plasticizer or the plasticizer composition and the dry point is referred to as time t for plasticizer absorption.

TABLE 3

Dryblend plasticizer absorption

| | Radical(s) in the trialkyl trimellitate (mixture) | Time t [min] for plasticizer absorption |
|---|---|---|
| Ester from Example 3 | n-hexyl | 4.9 |
| Trioctyl trimellitate ex Sigma Aldrich, purity 99% | 2-ethylhexyl | 9.0 |
| Ester mixture from Example 4* | 2-methylbutyl/n-pentyl Molar ratio 0.20:0.80 | 4.1 |
| Ester mixture from Example 5* | 2-methylbutyl/n-pentyl Molar ratio 0.50:0.50 | 4.4 |
| Ester mixture from Example 6* | 2-methylbutyl/3-methylbutyl/n-pentyl Molar ratio 0.33:0.33:0.34 | 4.5 |
| Ester mixture from Example 7* | 2-methylbutyl/n-pentyl Molar ratio 0.79:0.21 | 4.6 |
| Vestinol 9 ex Evonik Industries, purity >99% | Comparative substance: diisononyl phthalate (DINP) | 5.4 |

*inventive

In the case of the inventive mixtures of triisopentyl esters of trimellitic acid from Examples 4*, 5*, 6* and 7*, homogeneous dryblends were formed within a shorter time than in the case of diisononyl phthalate, the tri-n-hexyl ester of trimellitic acid (from Example 3) and the tri-2-ethylhexyl ester of trimellitic acid. It can be concluded directly from this that mixtures according to the invention have better processability with PVC than DINP, than the tri-n-hexyl ester of trimellitic acid and than the tri-2-ethylhexyl ester of trimellitic acid. Moreover, it can be inferred from the values in Table 3 that processability with PVC in mixtures according to the invention rises with the proportion of linear pentyl radicals in the pentyl radicals incorporated in the ester mixture.

The tri-2-ethylhexyl ester of trimellitic acid has a particularly high plasticizer absorption time and is therefore unsuitable as a plasticizer for numerous PVC applications, which is the reason why the migration properties thereof were not determined hereinafter.

Example 10: Determination of Migration Properties

The test for determination of the migration properties of a test specimen comprising a plasticizer or a plasticizer composition allows conclusions as to how plasticizer-containing formulations behave in application on direct contact with other materials—for example on contact between a plasticized PVC layer and a rigid PVC layer (called "multilayer systems"). If, for example, plasticizer migrates within an article from a plasticized polymer-containing component to a non-plasticized polymer-containing component, this can lead to unwanted embrittlement of the plasticized component and softening of the non-plasticized component, which can lead to leaks, declining stability and reduced service life of the article. Accordingly, a low migration tendency is an important property for a plasticizer usable in numerous applications or a corresponding component of a plasticizer composition.

The migration tendency of the inventive mixtures of triisopentyl esters of trimellitic acid and the comparative substances DINP, tri-n-butyl trimellitate, tri-n-pentyl trimellitate and tri-n-hexyl trimellitate was determined as follows:

The press plaques of thickness 1 mm produced in Example 8 were cut into blanks of 100 mm·100 mm and stored at 23° C. for 24 hours before their mass was determined.

In accordance with the method DIN EN ISO 177 (published 1999), the blanks were positioned between two contact sheets (Example 10.1: high-impact polystyrene (HIPS) (manufacturer: VINK Kunststoffe; 100×100×2 mm plaques); Example 10.2: non-plasticized PVC (rPVC) (manufacturer: VINK Kunststoffe; 100×100×2 mm plaques)) which had the same dimensions as the blanks apart from a thickness of 2 mm, and two of the layer constructions that arise in this way were stacked one on top of the other. These stacks each comprising blanks of the same plasticizer, weighted down with a weight of 2 kg, were stored in an oven (70(+/−1)° C.) for 28 days.

After 14 days and after 28 days, the loss of weight of each blank was determined (percent weight loss based on the original weight). After the first measurement, the stacks were reassembled again as before.

Table 4 shows the averaged values of the weight loss of the test specimens.

TABLE 4

Migration into high-impact polystyrene (HIPS) after 14 and 28 days

| Blank contains ... | Radical(s) in the trialkyl trimellitate (mixture) | Difference in weight after 14 days in % | Difference in weight after 28 days in % |
|---|---|---|---|
| Ester from Example 1 | n-butyl | 5.8 | 8.0 |
| Ester from Example 2 | n-pentyl | 5.1 | 6.9 |
| Ester from Example 3 | n-hexyl | 3.7 | 5.6 |
| Ester mixture from Example 4* | 2-methylbutyl/n-pentyl Molar ratio 0.20:0.80 | 3.6 | 5.5 |
| Ester mixture from Example 5* | 2-methylbutyl/n-pentyl Molar ratio 0.50:0.50 | 2.0 | 3.2 |
| Ester mixture from Example 6* | 2-methylbutyl/3-methylbutyl/n-pentyl Molar ratio 0.33:0.33:0.34 | 2.5 | 3.7 |
| Ester mixture from Example 7* | 2-methylbutyl/n-pentyl Molar ratio 0.79:0.21 | 1.6 | 2.7 |
| Vestinol 9 ex Evonik Industries, purity >99% | Comparative substance: diisononyl phthalate (DINP) | 11.2 | 14.6 |

*inventive

TABLE 5

Migration into rigid PVC (rPVC) after 14 and 28 days

| Blank contains ... | Radical(s) in the trialkyl trimellitate (mixture) | Difference in weight after 14 days in % | Difference in weight after 28 days in % |
|---|---|---|---|
| Ester from Example 1 | n-butyl | 9.3 | 11.7 |
| Ester from Example 2 | n-pentyl | 9.0 | 11.3 |
| Ester from Example 3 | n-hexyl | 8.0 | 10.1 |
| Ester mixture from Example 4* | 2-methylbutyl/n-pentyl Molar ratio 0.20:0.80 | 6.2 | 8.3 |
| Ester mixture from Example 5* | 2-methylbutyl/n-pentyl Molar ratio 0.50:0.50 | 5.9 | 7.9 |
| Ester mixture from Example 6* | 2-methylbutyl/3-methylbutyl/n-pentyl Molar ratio 0.33:0.33:0.34 | 7.4 | 9.4 |
| Ester mixture from Example 7* | 2-methylbutyl/n-pentyl Molar ratio 0.79:0.21 | 5.6 | 7.5 |
| Vestinol 9 ex Evonik Industries, purity >99% | Comparative substance: diisononyl phthalate (DINP) | 7.7 | 9.7 |

*inventive

It is apparent from Tables 4 and 5 that the inventive mixtures of triisopentyl esters of trimellitic acid consistently have a lower tendency to migrate than DINP and n-butyl, n-pentyl and n-hexyl triesters of trimellitic acid. In addition, it can be inferred from a comparison of the measurements for the blanks comprising the inventive ester mixtures from Examples 5, 6 and 8 that the migration tendency of the mixtures according to the invention decreases with rising proportion of the branched pentyl radicals in the pentyl radicals incorporated in the ester mixture. As the comparison of the measurements for the blanks comprising inventive ester mixtures from Examples 5 to 7 shows, a high proportion of 2-methylbutyl radicals in the branched isomeric pentyl radicals incorporated in the ester mixture has a positive effect on a low migration tendency.

European patent application 15187128.2 filed Sep. 28, 2015, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:
1. A composition, comprising:
   trialkyl esters of trimellitic acid;
   wherein the trialkyl radicals of the trialkyl esters are a mixture of isomeric pentyl radicals, wherein more than 5 mol % of the isomeric pentyl radicals are branched, and
   at least 50 mol % of the branched isomeric pentyl radicals are 2-methylbutyl radicals.
2. The composition according to claim 1, wherein at least 15 mol %, of the isomeric pentyl radicals of the trialkyl ester groups are branched.
3. The composition according to claim 1, wherein more than 10 mol % and less than 95 mol % of the isomeric pentyl radicals are linear.
4. A process for preparing the composition according to claim 1, comprising:
   reacting trimellitic acid and/or a trimellitic acid derivative with a mixture of isomeric pentanols;
   wherein more than 5 mol % of the isomeric pentyl radicals in the mixture of isomeric pentanols are branched isomeric pentyl radicals, and
   at least 50 mol % of the branched isomeric pentyl radicals are 2-methylbutyl radicals.
5. The process according to claim 4, wherein, during the reacting, the reaction mixture containing the trimellitic acid and/or the trimellitic acid derivative is heated to boiling and, after attaining boiling temperature, adding at least 0.2 molar equivalent of the amount of mixture of isomeric pentanols needed to introduce all the isomeric pentyl radicals incorporated in the ester mixture.
6. The process according to claim 4, wherein
   at least one isomerically pure tripentyl ester of trimellitic acid and at least one mixture of triisopentyl esters of trimellitic acid comprising isomeric pentyl radicals are mixed with one another, such that more than 5 mol % of the isomeric pentyl radicals are branched, and at least 50 mol % of the branched isomeric pentyl radicals are 2-methylbutyl radicals.
7. A plasticizer, or a plasticizer composition comprising the composition according to claim 1 and at least one further polymer-plasticizing compound.
8. A plasticizer composition comprising the composition according to claim 1 and at least one further polymer-plasticizing compound selected from the group consisting of alkyl benzoates, dialkyl adipates, glycerol esters, trialkyl citrates, acylated trialkyl citrates, glycol dibenzoates, trimellitates having radicals different from the isomeric pentyl radicals of claim 1, dialkyl terephthalates, dialkyl phthalates, esters of furandicarboxylic acid, dialkanoyl esters of dian- hydrohexitols, epoxidized fatty acid alkyl esters, polyadipates, and dialkyl esters of cyclohexane-1,2-, -1,3- or -1,4-dicarboxylic acid.

9. A polymer composition comprising the composition according to claim 1 wherein the polymer composition comprises one or more polymers selected from the group consisting of polyvinyl chloride, copolymers of vinyl chloride with vinyl acetate or with butyl acrylate, polyalkyl methacrylate (PAMA), polyvinyl butyral (PVB), chlorosulphonated polyethylene, polyurethane, polysulphides, polylactic acid (PLA), polyhydroxybutyral (PHB) and nitrocellulose.

10. A polyvinyl chloride polymer (PVC) or a PVC copolymer comprising the composition of claim 1.

11. A plasticized product comprising the composition of claim 1, wherein the product is selected from the group consisting of adhesives, sealing compounds, coating materials, paints, inks, plastisols, foams, synthetic leather, floor coverings, roofing membranes, underbody protection, fabric coatings, cables, wire insulation, hoses, extruded articles, films, automotive interior, wall coverings, liquid inks, toys, contact sheets, food packaging or medical articles.

* * * * *